United States Patent [19]

Rupprecht et al.

[11] Patent Number: 4,975,457

[45] Date of Patent: Dec. 4, 1990

[54] TRANS 2,3-DISUBSTITUTED-2,3-DIHYDRO-5-HYDROXY-BENZOFURANS AS INHIBITORS OF LEUKOTRIENE BIOSYNTHESIS

[75] Inventors: Kathleen M. Rupprecht, Cranford, N.J.; Joshua S. Boger, Concord, Mass.

[73] Assignee: Merck & Co., Inc., Rahway, N.J.

[21] Appl. No.: 411,788

[22] Filed: Sep. 25, 1989

[51] Int. Cl.$^5$ .................... A61K 31/34; C07D 307/80
[52] U.S. Cl. .................... 514/469; 549/20; 549/458; 549/462
[58] Field of Search ............... 549/462, 458; 514/468, 514/469

[56] References Cited

U.S. PATENT DOCUMENTS

| 3,337,563 | 8/1967 | Skaletzky et al. | 260/294.7 |
| 4,537,903 | 8/1985 | Chang et al. | 514/456 |
| 4,563,476 | 1/1986 | Chang et al. | 514/459 |
| 4,663,347 | 5/1987 | Atkinson et al. | 514/467 |
| 4,686,235 | 8/1987 | Chang et al. | 514/520 |
| 4,713,393 | 12/1987 | Chang et al. | 514/469 |
| 4,745,127 | 5/1988 | Atkinson et al. | 514/469 |
| 4,857,516 | 8/1989 | Terao et al. | 549/470 |

OTHER PUBLICATIONS

K. Brannock, et al., J. Org. Chem., 29, 2579, (1964).

Primary Examiner—John M. Ford
Assistant Examiner—Bernard I. Dentz
Attorney, Agent, or Firm—Hesna J. Pfeiffer; William H. Nicholson; Curtis C. Panzer

[57] ABSTRACT

Certain trans-2,3-disubstituted-2,3-dihydro-5-hydroxybenzofurans are described. The synthesis involves an intramolecular Michael addition to yield the thermodynamic trans isomer. The compounds were found to be inhibitors of 5-lipoxygenase, an enzyme crucial to the biosynthesis of leukotrienes and useful for the treatment of various inflammatory diseases.

6 Claims, No Drawings

TRANS 2,3-DISUBSTITUTED-2,3-DIHYDRO-5-HYDROXY-BENZOFURANS AS INHIBITORS OF LEUKOTRIENE BIOSYNTHESIS

BACKGROUND OF THE INVENTION

The present invention relates to novel 2,3-disubstituted-2,3-dihydro-5-hydroxybenzofurans as anti-inflammatory agents, as well as, the synthetic routes to these compounds.

Several patents have been issued on related structural types, which are stated to have similar utility, as anti-inflammatory agents are listed as follows: substituted cinnamyl-2,3-dihydrobenzofurans (Chang et al., U.S. Pat. Nos. 4,537,903 and 4,686,235), 5-hydroxy-2,3-dihydrobenzofurans (Chang, et al., U.S. Pat. No. 4,563,476), substituted phenyl-2,3-dihydrobenzofurans (Chang et al., U.S. Pat. No. 4,713,393), phenylthiomethyl-6-hydroxy-2,3-dihydrobenzopyrans (Thompson, et al., U.S. Pat. No. 4,558,067) and benzofuran-2-carboxylic acid esters (Atkinson, et al. U.S. Pat. Nos. 4,663,347 and 4,745,127).

The invention hereto describes inhibitors which contain novel substitution patterns designed to enhance the binding to 5-lipoxygenase. None of the above mentioned compounds are among the ones claimed in this patent application.

The 5-lipoxygenase enzyme controls the metabolism of arachidonic acid to the class of compounds known as leukotrienes. Inhibition of 5-lipoxygenase enzyme therefore prevents the formation of leukotrienes and so or diminishes the adverse effects of these mediators in a mammalian subject.

The leukotrienes are a novel group of biologically active mediators derived from arachidonic acid through the action of the 5-lipoxygenase enzyme system. The leukotrienes play an important role in inducing allergic reactions, such as asthma, allergic bronchitis or allergic rhinitis in man.

There are two groups of leukotrienes derived from a common unstable precursor, Leukotriene $A_4$. The first of these are the peptido-lipid leukotrienes, the most important being leukotrienes $C_4$ and $D_4$. These compounds collectively account for the biologically active materials known as the slow reacting substances of anaphylaxis. They are potent in producing bronchoconstriction, increasing vascular permeability in the skin and in promoting mucous production.

The most important compound in the second group of leukotrienes is Leukotriene $B_4$, a dihydroxy fatty acid derived from Leukotriene $A_4$. $LTB_4$ stimulates leukocytes formation (chemotaxis and chemokinesis) induces an increase in capillary permeability and causes smooth muscle contractions, Leukotriene $B_4$ has chemotactic potency for macrophage and neutrophils at concentrations of 1 ng/mls. Both groups of leukotrienes are formed following oxygenation of arachidonic acid through the action of the 5-lipoxygenase enzyme. See D. M. Bailey et al., Ann. Rpts. Med. Chem. 17:203 (1982).

Leukotrienes can also mediate other disease states, these include psoriasis, atopic dermatitis, gouty arthritis and gall bladder spasms. They also may play a role in cardiovascular disease because Leukotrienes $C_4$ and $D_4$ act as coronary and cerebral arterial vasoconstrictors and these compounds may also have negative ionotropic effects on the myocardium. In addition, the leukotrienes are important mediators of inflammatory diseases through their ability to modulate leukocyte and lymphocyte function. See B. Samuelsson, Science 220: 568 (1983).

Finally, the invention provides novel compounds with the general structure shown in Formula I that act as inhibitors of the mammalian 5-lipoxygenase enzyme system, thus preventing the biosynthesis of the leukotrienes $B_4$, $C_4$, $D_4$ and $E_4$.

DETAILED DESCRIPTION OF THE INVENTION

A Scope of the Invention

This invention relates to novel compounds of Formula I:

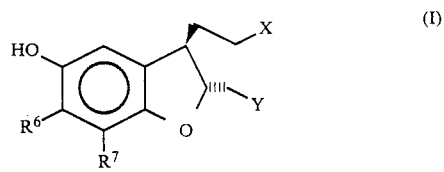

(I)

wherein:
$R^6$ is:
  $(C_3-C_6)$-1-alk-2-ene, or
  $(C_3-C_6)$-alkyl; and
$R^7$ is:
  H; or
  $R^7$ and $R^6$ can join to form ring wherein the ring is defined as a 6-membered saturated unsaturated or aromatic ring containing a carbon framework; and
X is:
  H,
  alkyl (especially, $(C_1-C_6)$ alkyl),
  alkoxyl,
  alkoxyalkylether,
  mercaptoalkyl, or
  halo; and
Y is:
  $(C_1-C_6)$-haloalkyl, methoxymethyloxy-$(C_1-C_6)$-alkyl,
  $(CH_2)_nCO_2CH_3$ where n=0, 1, 2, 3, 4 or 5,
  $(C_1-C_6)$-alkyl, or
  $(C_1-C_6)$-hydroxyalkyl; and or pharmaceutically acceptable salts thereof.

In a preferred embodiment of the instant invention, the compounds of Formula (I)
$R^6$ is $CH_2CH=CH_2$, or $CH_2CH_2CH_3$; and
$R^7$ is H; and
X is:
  $(C_1-C_6)$-alkyl, or phenoxy; and
Y is:
  methoxycarbonyl,
  hydroxymethylene,
  chloromethylene,
  methyl,
  2-(1,3-dithiane), or
  methoxymethyloxymethylene; and Specific species of the preferred embodiment are shown in the table below:

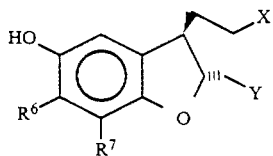

| $R^6$ | $R^7$ | X | Y |
|---|---|---|---|
| $CH_2CH=CH_3$ | H | $CH_2CH_3$ | $CO_2CH_3$ |
| $CH_2CH_2CH_3$ | H | $CH_2CH_3$ | $CO_2CH_3$ |
| $CH_2CH=CH_2$ | H | OPh | $CO_2CH_3$ |
| $CH_2CH_2CH_3$ | H | OPh | $CO_2CH_3$ |
| $CH_2CH=CH_2$ | H | OPh | ![dithiane] |
| $CH_2CH_2CH_3$ | H | OPh | ![dithiane] |
| $CH_2CH=CH_2$ | H | $CH_2CH_3$ | $CH_2OH$ |
| $CH_2CH_2CH_3$ | H | $CH_2CH_3$ | $CH_2OH$ |
| $CH_2CH=CH_2$ | H | $CH_2CH_3$ | $CH_2Cl$ |
| $CH_2CH_2CH_3$ | H | $CH_2CH_3$ | $CH_2Cl$ |
| $CH_2CH=CH_2$ | H | $CH_2CH_3$ | $CH_3$ |
| $CH_2CH_2CH_3$ | H | $CH_2CH_3$ | $CH_3$ |
| $CH_2CH_2CH_3$ | H | $CH_2CH_3$ | $CH_2OCH_2OCH_3$. |

The compounds of the present invention are conveniently prepared using the procedures described generally in the two schemes below and more explicitly in the specific Examples thereafter.

The aldehyde, shown in Scheme 1, is reacted with a secondary amine such as piperidine, pyrrolidine, dimethylamine or diethyl amine, in the presence of an organic sulfonic acid, such as p-toluenesulfonic acid, to generate the corresponding enamine. The enamine can then be treated with benzoquinone and alkylated with 1-bromo-2-propene and an alkoxide or an amine followed by silica gel chromatography to hydrolyze the animal and give the desired 5-(2-propenyloxy)-2-hydroxy-3-substituted-2,3-dihydro benzofuran A (Skaletzky, L. L. U.S. Pat. No. 3,317,527, 1967; Skaletzky, L. L. U.S. Pat. No. 3 337 563, 1967; Skaletzky, L. L. U.S. Pat. No. 3,496,181, 1968). This lactol intermediate A can then be treated with an appropriate stabilized Wittig reagent to afford the desired alkene, which under basic conditions will cyclize to the 5 (2-propenyloxy)-2,3-disubstituted 2,3-dihydro-benzofuran B. The Wittig reagent maybe prepared using triphenylphosphine, an alkylhalide and an alkoxide to generate the (triphenylphosphoranylidene)alkane or it maybe commercially available.

The allyl ether in B upon treatment with a Lewis acid such as $BCl_3$ or $AlCl_3$, in a chlorinated solvent or simply with heat yields the Claisen rearrangement product C. Catalytic hydrogenation to reduce the 2-propenyl group was accomplished using 5–10% Pd on carbon or another viable catalyst.

The allyl ether B may also be used, as shown in Scheme 2, as an intermediate in the reduction of the methyl carboxylate to the aldehyde or alcohol D using an alkyl metal hydride, such as diisobutylaluminum hydride. The alcohol D can be halogenated using for example, Lee's reagent ($Ph_3P$, $CX_4$, where X is Cl or Br) to give the halide E. The aldehyde can be protected as the 2-(1,3-dithiane) using 1,3 propanedithiol and borontrifluoride to give compound G. The halide E can be alkylated with the appropriate carbanion or reduced with superhydride to dehalogenate to give compound F.

SCHEME 1

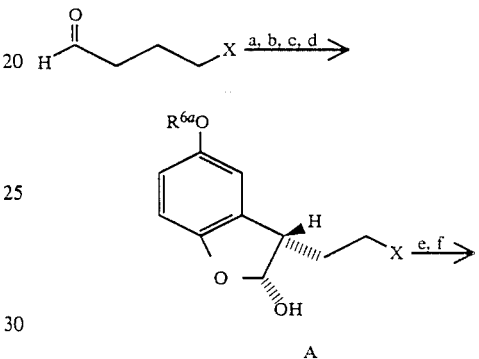

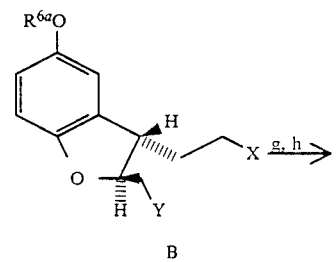

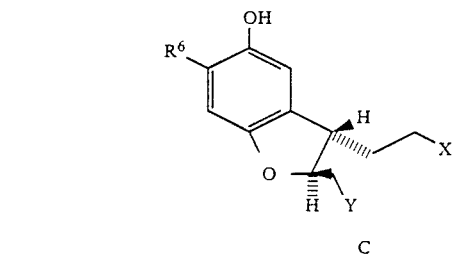

The substituents in Scheme 1 are generally defined:
$R^{6a}$ is H or ($C_3$–$C_6$)-1-alk-2-ene;
$R^6$ is $R^{6a}$ or ($C_3$–$C_6$)- alkyl;
X is as defined in the detailed description of Formula I,
$R^7$ is H, or $R^6$ and $R^7$ are joined to form a benzene ring and $R^{6a}$ is hydrogen, in this case Step b will employ 1,4-naphthoquinone and the final step used to prepare compound C will be omitted, and
Y is generally a $(CH_2)_nCO_2CH_3$, where n=1,2,3,4, or 5, which can be further elaborated to the other definitions of Y as shown in Scheme 2.

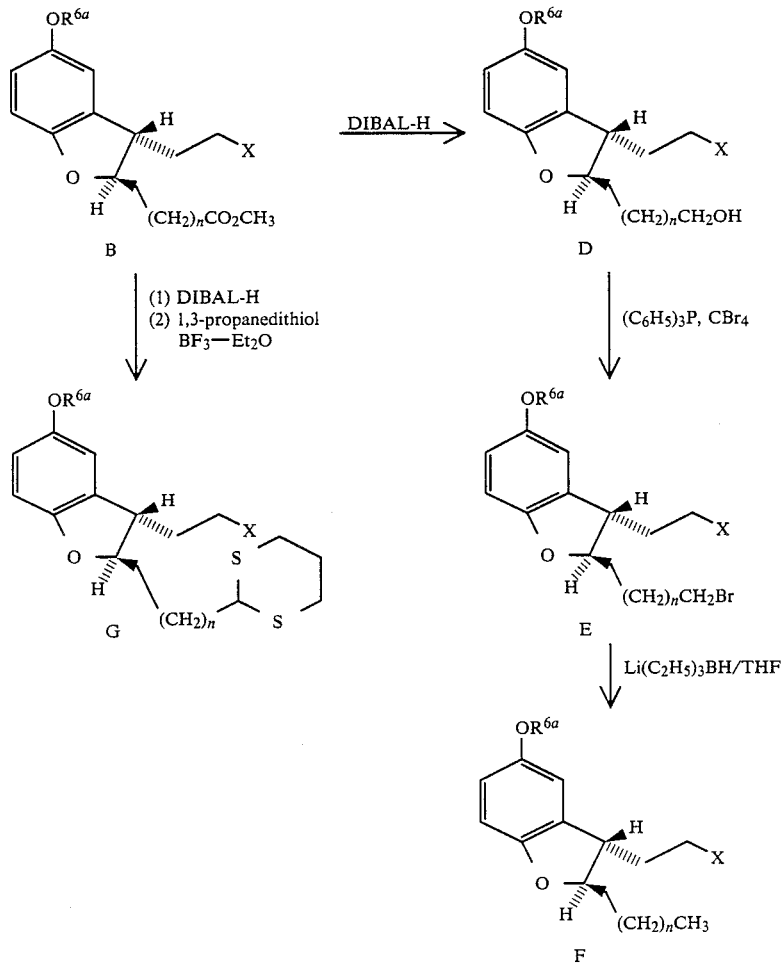

SCHEME 2

Compound E can be elaborated using a variety of methods known by one skilled in the art.

B Utility of the Subject Compounds of the Invention

This invention also relates to a method of treating inflammation in patients in need of such treatment. Generally, an effective non-toxic amount of a compound of Formula (I) or a pharmaceutical composition thereof, particularly an especially preferred compound, is administered to the patient as the active constituent.

To demonstrate the utility of the present invention, representative novel compounds of formula I were evaluated for their ability to inhibit the production of leukotriene B$_4$ (LTB$_4$) in isolated rat and human polymorphonuclear leukocytes (PMN). Other compounds known to inhibit leukotriene biosynthesis have been shown to have activity in this assay, and thus the assay is of value in predicting in vivo activity. Thereby useful in determining the dosage and route of administration.

For the treatment of inflammation, arthritis conditions, psoriasis, asthma, or other diseases mediated by prostaglandins, a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelation or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut (arachis) oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinyl pyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial ester derived from fatty acids and hexitol anhydrides, for example, polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules are suitable for the preparation of an aqueous suspension by mixing them with water. They provide the active ingredient in admixture with a dispersing or wetting agent, a suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally occurring gums, for example, gum acacia or gum tragacanth, naturally-occurring phosphatides, for example, soy bean, lecithin, and esters or partial ester derived from fatty acids and hexitol anhydrides, for example, sorbitan mono-oleate, and condensation products of the said partial esters with enthylene oxide, for example, polyoxyethylene sorbitan monooleate.

An ointment containing the pharmaceutical compositions of the present invention ma be prepared, among other methods known in the art, by combining the active ingredient with a medium consisting of a glycol, a lower alkanol, and water; a gelling agent; and optionally an adjuvant such as diisopropyl adipate, diethyl sebacate, ethyl caproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

The preferred route of administration is an oral route, with the exception of treating a skin disorder, such as psoriasis, where the preferred route of administration would typically be a topical route. In oral administration the drug can be employed in any of the usual dosage forms such as tablets, capsules, solutions, suspensions or powders, either in a contemporanious delivery or sustained release form. Any number of the usual excipients or tableting aids can likewise be included.

Dosage levels of the order to 0.2 mg to 140 mg per kilogram of body weight per day are useful in the treatment of the above-indicated condition (10 mg to 7 gms per patient per day). For example, inflammation is effectively treated by the administration from about 0.5 to 50 mg of the compound per kilogram of body weight per day (25 mg to 5 mgs per patient per day).

The amount of active ingredient that may be combined with the carrier materials to produce a single dosage will vary depending upon the host treated and the particular mode of administration. Dosage unit forms will generally contain from about 25 mg to about 1 g of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Representative compounds of Formula I have been tested using the following two assays described below:

A. Preparation of Human PMN. Human blood is obtained by antecubital venepuncture from consenting volunteers who denied having taken medication within the previous 7 days. The blood is immediately added to 10% (v/v) trisodium citrate (0.13M) or 5% (v/v)sodium heparin (1000 IU/mL). PMNs are isolated from anticoagulated blood by dextran sedimentation and centrifugation through Ficoll-Hypaque (specific gravity 1.077), essentially as described by Boyum. (Boyum, A., Scand. J. Clin. Lab. Invest. 1968, 21 (Supp 97), 77). Contaminating erthrocytes are removed by lysis following exposure to ammonium chloride (0.16M) in Tris buffer (pH 7.65), and the PMNs resuspended at $5 \times 10^5$ cells/mL in HEPES (15 mM) buffered Hanks balanced salt solution containing $Ca^{2+}$ (1.4 mM) and $Mg^{2+}$ (0.7 mM), pH 7.4. Viability is assessed by Trypan blue exclusion and is typically greater than 98%.

B. Rat Peritoneal Polymorphonuclear leukocytes (PMN). Male Sprague-Dawley rats were purchased from Taconic Farms, Germantown, N.Y. The animals were maintained on standard pellet diet and water ad lib. Elicited PMN were prepared from peritoneal exudates as follows: 8 ml of 12% sodium caseinate was injected intraperitoneally into male rats. After 18-20 hours, the rats were killed with $CO_2$ and the peritoneal cavities were lavaged with Eagle's MEM (pH 7.7) without $NaHCO_3$ but containing Earle's salts, L-glutamine, and 30 mM HEPES. The PMN were isolated by centrifugation, washed with MEM, filtered through lens paper to remove clumps, and adjusted to a concentration of $1 \times 10^7$ cells/ml.

The following examples illustrate the preparation of the compounds of the formula (I) and as such are not to be considered as limiting the invention set forth in the claims appended hereto.

EXAMPLE 1

Methyl(2R*,3S*)-(3-Butyl-2,3-dihydro-5-hydroxy-6-(2-propenyl)-2-benzofuranyl)acetate Step A: Preparation of (2S*,3S*)-3-Butyl-2-hydroxy-5-(2-prorenyloxy)-2 3-dihydrobenzofuran Samples of 6.00 g (60 mmole) of hexanal and 7.0 mL (70 mmole) of piperidine were added to 100 mL of benzene in a 500 mL round bottom flask that had been fitted with a Dean Stark condenser. Then 0.500 g (2.90 mmole) of p-toluenesulfonic acid was added and the solution was heated at reflux for 4 h, until all the water had been removed. The solution was concentrated under reduced pressure and the residue was dissolved in 75 mL of dry benzene. This solution was added dropwise to a 1000 mL flask containing a rapidly stirring solution of 6.00 g (60 mmole) of 1,4-benzoquinone in 100 mL dry benzene. The solution became warm during the addition; a white solid developed and the liquid fraction became dark red in color. TLC of the reaction mixture (20% ethyl acetate-hexane) indicated that all of the benzoquinone had been consumed after 4 h. The solid was dissolved by addition of 300 mL of THF and the solution was cooled to 0° C. in an ice bath. Then 20.2 g (180 mmole) of potassium t-butoxide and 13.2 g(180 mmole) of allyl bromide were added and the mixture was stirred at room temperature for 24 h. The solution was partitioned between ether and water and the aqueous layer was washed with two portions of ether. The ether extracts were sequentially washed with 1M HCl, then saturated $NaHCO_3$ solution and saturated NaCl solution. The combined extracts were dried over magnesium sulfate and concentrated to a dark brown oil. The residue was purified by flash chromatography (12 cm column) using 20% ethyl acetate-hexane to afford 10.8 g (73%) of a pale orange oil. Attempts at distillation of this material resulted in thermally induced Claisen rearrangement of the allyl phenyl ether; $^1H$ NMR (200 MHz, $CDCl_3$, w): 0.92 (t, J=7 Hz, 3H), 1.36 (m, 4H), 1.56 (m, 1.75H, trans isomer), 1.78 (m, 0.25 H, cis isomer), 3.08 (dt, J=6.5, 2 Hz, 0.85 H, trans isomer), 3.28 (dt, J=6.5, 6 Hz), 4.46 (dt, J=5.5, 1.5 Hz, 2H), 5.26 (dq, J=10.5, 1.5 Hz, 1H), 5.38 (dq, J=17, 1.5 Hz, 1H), 5.61 (d, J=2 Hz, 0.85 H, trans isomer), 5.89 (d, J=6 Hz, 0.15 H, cis isomer), 6.03 (ddt, J=17, 10.5, 5.5 Hz, 1H), 6.72 (m, 2H), 6.80 (m, 1H); EI mass spectrum, (m/e): 248 (22, M+), 208 (50), 189 (10), 163 (14), 147 (16), 123 (24), 98 (100), 77 (10), 57 (20), 55 (42).

Step B: Preparation of Methyl (2S*,3S*)-4-(2 hydroxy-5-(2-propenyloxy)phenyl)-2-octenoate A solution of 2.48 g (10.0 mmole) of (Example 1, Step A) and 7.14 g (20 mmole) of methyl (triphenylphosphoranylidene)acetate in 30 mL THF was heated at reflux. After 3 h all of the starting material had been consumed and the solution was concentrated under reduced pressure. The residue was taken up in ether and filtered to remove unreacted yield. The filtrate was concentrated and purified by flash chromatography (3 cm column) using 15% ethyl acetate-hexane to afford 2.61 g (86%) of a pale orange oil; $^1H$ NMR (200 MHz, $CDCl_3$,w): 0.87 (t, J=7 Hz, 3H), 1.30 (m, 4H), 1.75 (q, J=7 Hz, 2H), 3.72 (s, 3H), 3.80 (dq, J=7 Hz, 2H), 4.49 (dt, J=5.5, 1 Hz, 2H), 5.24 (ddt, J=10.5, 1.5, 1 Hz, 1H), 5.37 (ddt, J=17, 1.5, 1 Hz, 1H), 5.82 (dd, J=15.5, 2 Hz), 6.02 (ddt, J=17, 10.5, 1 Hz, 1H), 6.65 (m, 3H), 7.12 (dd, J=15.5, 7 Hz, 1H); FAB mass spectrum (m/e) 459 (100, M+matrix), 305 (12, M+H).

Step C: Preparation of Methyl (2R*,3S*)-(3 butyl-2,3-dihydro-5-(2-propenyloxy)-2-benzofuranyl)acetate A solution of 1.24 g (5.0 mmole) of (Example 1, Step B) and 0.5 mL (0.5 mmole) of piperidine in 10 mL methanol was heated at reflux. After 1 hour cyclization was complete by tlc (20% ethyl acetatehexane) and the solution was concentrated under vacuum and purified by flash chromatography (3 cm column) using 15% ethyl acetate-hexane to afford 1.17 g (94%) of a pale yellow oil; NMR (200 MHz, $CDCl_3$, w): 0.91 (t, J=7 Hz, 3H), 1.36 (m, 4H), 1.67 (m, 2H), 2.57 (AB, dd, J=16, 5.5 Hz, 1H), 2.73 (AB, dd, J=16, 7.5 Hz, 1H), 3.03 (dt, J=6, 5.5 Hz, 1H), 3.72 (s, 3H), 3.76 (s, 0.1 H, cis isomer $OCH_3$), 4.45 (dt, J=5.5, 1.5 Hz, 2H), 4.82 (ddd, J=7.5, 5.5, 5 Hz, 1H), 5.26 (dq, J=10.5, 1.5 Hz, 1H), 5.39 (dq, J=17, 1.5 Hz, 1H), 6.03 (ddt, J=17, 10.5, 5.5 Hz, 1H), 6.68 (m, 2H), 6.75 (m, 1H); FAB mass spectrum (m/e): 305 (100, M+H).

Step D: Methyl (2R*,3S*)-(3-butyl-2,3-dihydro-5-hydroxy-6-(2-propenyl)-2-benzofuranyl)acetate A solution of 1.50 g (5.0 mmol) of (Example 1, Step C) in 20 mL of $CH_2Cl_2$ was cooled to 0° C. under nitrogen. Then 5.0 mL of a 1M $BCl_3$ solution in $CH_2Cl_2$ was added dropwise and the solution was stirred at room temperature for 30 min. The reaction was quenched by addition of 10 mL of saturated $NaHCO_3$ solution and the mixture was partitioned between ether and water. The organic extract was washed with saturated $NaHCO_3$ solution and brine, dried over $MgSO_4$, and concentrated to an oil. This was purified by flash chromatography (3 cm column) using 10% ethyl acetate-hexane to afford 1.04 g (68%) of a colorless oil; $^1H$ NMR (200 MHz, $CDCl_3$, w) d 0.91 (t, J=7 Hz, 3H), 1.36 (m, 4H), 1.67 (m, 2H), 2.57 (AB, dd, J=16, 5.5 Hz, 1H), 2.73 (AB, dd, J=16, 7.5 Hz, 1H), 3.03 (dt, J=6, 5.5 Hz, 1H), 3.36 (m, 2H), 3.72 (s, 3H), 3.76 (s, 0.1 H, cis isomer $OCH_3$), 4.82 (ddd, J=7.5, 5.5, 5 Hz, 1H), 5.18 (m, 3H), 6.68 (s, 1H), 6.75 (s, 1H); FAB mass spectrum (m/e) 305 (100, M+H).

EXAMPLE 2

Methyl (2R*,3S*)-(3-butyl-2 3-dihydro 5-hydroxy-6-(2-prop)-2-benzofuranyl)acetate A solution of 0.250 g (0.816 mmol) of (Example 1, Step D) and 50 mg of 5% Pd/C in 10 mL of ethyl acetate was shaken under 40 psi $H_2$ for 1h. The solution was filtered through Celite and the filtrate concentrated to a colorless oil. This was purified by HPLC (silica gel, Whatman Magnum 20) using 10% ethyl acetate-hexane to afford 0.212 g (65%) of colorless oil; $^1$H NMR (200 MHz, CDCl$_3$,w): 0.91 (m,6H), 1.36 (m, 4H), 1.67 (m, 4H), 2.52 (t, J=7Hz, 2H), 2.57 (AB, dd, J=16, 5.5 Hz, 1H), 2.73 (AB, dd, J=16, 7.5 Hz, 1H), 3.03 (dt, J=6, 5.5 Hz, 1H), 3.72 (s, 3H), 3.76 (s, 0.1 H, cis isomer OCH$_3$), 4.82 (ddd, J=7.5, 5.5, 5 Hz, 1H), 6.68 (s, 1H), 6.75 (s, 1H); FAB mass spectrum (m/e): 307 (100, M+H).

EXAMPLE 3

Methyl(2R*,3S*) (2,3-dihydro-5-hydroxy-3-(2-phenoxyethyl)-6-(2-propenyl)-2 benzofuranyl) acetate

Preparation of (2S*,3S*)-2-Hydroxy-3-(2-phenoxyethyl)-5-(2-propenyloxy)-2,3-dihydrobenzofuran Samples of 8.21 g (50 mmole) of 4-phenoxybutanal and 10.0 mL (1000 mmole) of piperidine were added to 250 mL of benzene in a 500 mL round bottom flask that had been fitted with a Dean-Stark condenser. Then 0.500 g (2.90 mmole) of p-toluenesulfonic acid was added and the solution was heated at reflux for 4 h, until all the water had been removed. The solution was concentrated under reduced pressure and the residue was dissolved in 60 mL of dry benzene. This solution was added dropwise to a 1000 mL flask containing a rapidly stirring solution of 5.40 g (50 mmole) of 1,4-benzoquinone in 50 mL dry benzene. The solution became warm during the addition; a white solid developed and the liquid fraction became dark red in color. TLC of the reaction mixture (20% ethyl acetate-hexane) indicated that all of the benzoquinone had been consumed after 4 h. The solid was dissolved by addition of 100 mL of THF and the solution was cooled to 0° C. in an ice bath. Then 11.2 g (100 mmole) of potassium t-butoxide and 6 g (81 mmole) of allyl bromide were added and the mixture was stirred at room temperature for 24 h. The solution was partitioned between ether and water and the aqueous layer was washed with two portions of ether. The ether extracts were sequentially washed with 1M HCl, then saturated NaHCO$_3$ solution and saturated NaCl solution. The combined extracts were dried over magnesium sulfate and concentrated to a dark brown oil. The residue was purified by flash chromatography (12 cm column) using 20% ethyl acetate-hexane to afford 7.61 g (51%) of a pale orange oil. Attempts at distillation of this material resulted in thermally induced Claisen rearrangement of the allyl phenyl ether. $^1$H NMR (200 MHz, CDCl$_3$, w): 2.15 (t, J=7Hz, 2H), 3.40 (t, J=6 Hz), 4.15 (t, J=7 Hz, 2H), 4.46 (m, 2H), 5.26 (dq, J=10.5, 1.5 Hz, 1H), 5.38 (dq, J=17, 1.5 Hz, 1H), 5.61 (d, J=2 Hz, 0.85 H, trans isomer), 5.89 (d, J=6 Hz, 0.15 H, cis isomer), 6.03 (ddt, J=17, 10 5, 5.5 Hz, 1H), 6.75 6.80 (m, 2H), 6.95 (m, 3H), 7.30 (m, 2H); FAB mass spectrum (m/e) 301 (100, M+H).

Step B: Preparation of Methyl(2S*,3S*)-4-(2-hydroxy-5-(2-propenyloxy)-phenyl)-5-phenoxy-2-hexenoate A solution of 9.01 g (30.0 mmole) of (Example 3, Step A) and 21.4 g (60 mmole) of methyl (triphenylphosphoranylidene)acetate in 1000 mL THF was heated at reflux. After 2 h all of the starting material had been consumed and the solution was concentrated under reduced pressure. The residue was taken up in ether and filtered to remove unreacted ylid. The filtrate was concentrated and purified by flash chromatography (3 cm column) using 10% ethyl acetate-hexane to afford 9.24 g (84%) of a pale orange oil: $^1$H NMR (200 MHz, CDCl$_3$, w): 2.15 (t, J=7Hz, 2H), 3.72 (s, 3H), 3.80–4.2 (m, 3H), 4.49 (dt, J=5.5, 1 Hz, 2H), 5.24 (ddt, J=10.5, 1.5, 1 Hz, 1H), 5.37 (ddt, J=17, 1.5, 1 Hz, 1H), 5.82 (dd, J=15.5, 2 Hz), 6.02 (ddt, J=17, 10.5, 1 Hz, 1H), 6.65–7.0 (m, 5H) 7.12 (dd, J=15.5, 7 Hz, 1H), 7.30 (m, 2H); FAB mass spectrum (m/e): 367 (100, M+H).

Step C: Methyl (2R*,3S*)-(2,3-dihydro-3-(2-phenoxyethyl)-5-(2-propenyloxy)-2-benzofuranyl) acetate A solution of 1.24 g (5.0 mmole) of (Example 3, Step B) and 0.5 mL (0.5 mmole) of piperidine in 10 mL methanol was heated at reflux. After 1 h cyclization was complete by tlc (20% ethyl acetate-hexane) and the solution was concentrated under vacuum and purified by flash chromatography (3 cm column) using 15% ethyl acetate-hexane to afford 1.17 g (94%) of a pale yellow oil; $^1$H NMR (200 MHz, CDCl$_3$,w): 2.15 (t, J=7Hz, 2H), 2.57 (AB, dd, J=16, 5.5 Hz, 1H), 2.73 (AB, dd, J=16, 7.5 Hz, 1H), 3.3 (m, 1H), 3.72 (s, 3H), 4.11 (t, J=7Hz, 2H), 4.45 (dt, J=5.5, 1.5 Hz, 2H), 4.95 (ddd, J=7.5, 5.5, 5 Hz, 1H), 5.26 (dq, J=10.5, 1.5 Hz, 1H), 5.39 (dq, J=17, 1.5 Hz, 1H), 6.03 (ddt, J=17, 10.5, 5.5 Hz, 1H), 6.68 (m, 2H), 6.75 (m, 1H) 6.90 (m, 3H), 7.30 (m, 2H); FAB mass spectrum, (m/e): 367 (100, M+H).

Step D: Methyl (2R*,3S*) (2,3-dihydro-5-hydroxy-3-(2-phenoxyethyl)-6-(2-propenyl)-2-benzofuranyl)acetate A solution of 2.56 g (7.0 mmol) of (Example 3, Step C) in 25 mL of CH$_2$Cl$_2$ was cooled to 0° C. under nitrogen. Then 7.5 mL of a 1M BCl$_3$ solution in CH$_2$Cl$_2$ was added dropwise and the solution was stirred at room temperature for 45 min. The reaction was quenched by addition of 15 mL of saturated NaHCO$_3$ solution and the mixture was partitioned between ether and water. The organic extract was washed with saturated NaHCO$_3$ solution and brine dried over MgSO$_4$, and concentrated to an oil. This was purified by flash chromatography (3 cm column) using 20% ethyl acetate-hexane to afford 2.15 g (84%) of a colorless oil; $^1$H NMR (200 MHz, CDCl$_3$, w): 2.15 (t, J=7Hz,2H), 2.57 (AB, dd, J=16, 5.5 Hz, 1H), 2.73 (AB, dd, J=16, 7.5 Hz, 1H), 3.36 (m, 3H), 3.72 (s, 3H), 4.11 (t, J=7Hz, 2H), 4.95 (ddd, J=7.5, 5.5, 5 Hz, 1H), 5.18 (m, 3H), 6.68 (s, 1H), 6.75 (s, 1H) 6.90 (m, 3H), 7.30 (m, 2H); FAB mass spectrum (m/e) 367 (100, M+H).

Example 4

Methyl(2R*,3S*)-(2,3-dihydro-5-hydroxy-3-(2-phenoxyethyl)-6-propyl-2-benzofuranyl)acetate A solution of 0.250 g (0.682 mmol) of (Example 3, Step D) and 50 mg of 5% Pd/C in 6 mL of ethyl acetate was shaken under 40 psi H2 for 45 min. The solution was filtered through Celite and the filtrate concentrated to a colorless oil. This was purified by HPLC (silica gel, Whatman Magnum 20) using 10% ethyl acetate-hexane to afford 0.213 g (85%) of colorless oil; $^1$H NMR (200 MHz, CDCl$_3$, w): 0.97 (t, J=7Hz, 3H), 1.62 (m, 2H), 2.15 (t, J=7Hz, 2H ), 2.52 (t, J=6 Hz, 2H), 2.57 (AB, dd, J=16, 5.5 Hz, 1H), 2.73 (AB, dd, J=16, 7.5 Hz, 1H), 3.36 (m, 1H), 3.72 (s, 3H), 4.11 (t, J=7Hz, 2H), , 4.95 (ddd, J=7.5, 5.5, 5 Hz, 1H), 6.68 (s, 1H), 6.75 (s, 1H) 6.90 (m, 3H), 7.30 (m, 2H) ; FAB mass spectrum (m/e): 369 (100, M+H).

EXAMPLE 5

Preparation of (2S*,3S*)-3-Butyl-2,3-dihydro-2-(2-hydroxyethyl)-5-(2-propenyloxy)benzofuran

Step A: Preparation of (2S*,3S*)-3-Butyl-2,3-dihydro-2-(2-hydroxyethyl)-5-(2-propenyloxy)benzofuran A solution of 3.04 g (10 mmol) of (Example 1, Step C) in 20 mL of toluene was cooled to −78° C. Then 20 mL (30 mmol) of 1.5M DIBAL-H in toluene was added and the solution was stirred at −78° C. for 2h and allowed to warm to room temperature for 2h. The reaction was quenched with 20 mL of 2M HCl and the mixture was partitioned between ethyl acetate and water. The organic layer was washed with 2M HCl, saturated NaCl solution, dried over MgSO$_4$, and concentrated. The residue was chromatographed on silica gel using 30% ethyl acetate-hexane to give 1.62 g (59%) of a colorless oil; $^1$H NMR (200 MHz, CDCl$_3$, w): d 0.91 (t, J=7 Hz, 3H), 1.36 (m, 4H), 1.67 (m, 4H), 2.70 (s, 1H), 3.03 (dt, J=6, 5.5 Hz, 1H), 3.75 (t, J=6Hz, 2H), 4.45 (dt, J=5.5, 1.5 Hz, 2H), 4.82 (ddd, J=7.5, 5.5, 5 Hz, 1H), 5.26 (dq, J=10.5, 1.5 Hz, 1H), 5.39 (dq, J=17, 1.5 Hz, 1H), 6.03 (ddt, J=17, 10.5, 5.5 Hz, 1H), 6.68 (s, 1H), 6.75 (s, 1H); FAB mass spectrum (m/e): 277 (100, M+H).

Step B: Preparation of (2S*,3S*) 3-Butyl 2,3-dihydro-2-(2 hydroxyethyl)-5-hydroxy-6-(2-propenyl)benzofuran A solution of 1.50 g (5.42 mmol) of (Example 5, Step A) in 20 mL of CH$_2$Cl$_2$ was cooled to 0° C. Then 6 mL of a 1.0M solution of BCl$_3$ in CH$_2$Cl$_2$ was added and the solution was stirred at room temperature for 1h. The reaction was quenched with 20 mL of saturated NaHCO$_3$ solution and the mixture was partitioned between ether and water. The aqueous layer was washed with ether and the ether layers were washed sequentially with NaHCO$_3$ solution and saturated NaCl solution. The combined organic extracts were dried over MgSO$_4$ and concentrated to afford 1.53 g (100%) of a colorless oil; hu 1H NMR (200 MHz, CDCl$_3$, w) 0.91 (t, J=7 Hz, 3H), 1.36 (m, 4H), 1.67 (m, 4H), 2.70 (s, 1H), 3.03 (dt, J=6, 5.5 Hz, 1H), 3.40 (m, 2H), 3 75 (t, J=6Hz, 2H), 4.82 (ddd, J=7.5, 5.5, 5 Hz, 1H), 5.20 (m, 3H), 6.68 (m, 2H), 6.75 (m, 1H); FAB mass spectrum (m/e) 277 (100, M+H).

EAMPLE 6

(2S*,3S*)-3-Butyl-2,3-dihydro-2-(2-hydroxyethyl)-5-hydroxy-6-propylbenzofuran

A solution of 0.250 g (0.904 mmol) of (Example 5, Step B) and 50 mg of 5% Pd/C catalyst in 10 mL of ethyl acetate was shaken under 40 psi H$_2$ for 4 h. The solution was filtered through Celite and concentrated to an homogeneous pale yellow oil; $^1$H NMR (200 MHz, CDCl$_3$, w): 0.91 (m, 6H), 1.36 (m, 4H), 1.67 (m, 6H), 2.50 (t, J=7Hz, 2H), 2.70 (s, 1H), 3.03 (dt, J=6, 5.5 Hz, 1H), 3.75 (t, J=6Hz, 2H), 4.82 (ddd, J =7.5, 5.5, 5 Hz, IH), 6.68 (s, 1H), 6.75 (s, 1H); FAB mass spectrum (m/e): 277 (100, M+H). FAB mass spectrum: (m/e): 279 (100, M+H).

EXAMPLE 7

(2S*,3S*) 2-(-2,3-dihydro 2-(1,3-dithianylmethyl)-3-(2-phenoxyethyl)-5-(2-propenyl)benzofuran

Step A: Preparation of (2S*,3S*)-2(-2,3-dihydro-2-(1,3-dithianylmethyl)-3-(2-phenoxyethyl)-5-(2-propenyloxy)benzofuran A solution of 0.735 g (2.0 mmol) of (Example 3, Step C) in 5 mL of toluene was cooled to −78° C. Then 1.5 mL of a 1.5M DIBAL-H solution was added dropwise and the solution was stirred at −78° C. for 1h. The reaction was quenched by dropwise addition of 2M methanolic HCl and the mixture was partitioned between ether and 0.5M HCl. The ether layer was washed with saturated NaHCO$_3$ solution and saturated NaCl solution, dried over MgSO$_4$, and concentrated. A solution of the oily residue and 1 mL of 1,3-propanedithiol in 5 mL CH$_2$Cl$_2$ was cooled to 0° C. and 2.5 mL of a 1M BF$_3$-etherate solution in CH$_2$Cl$_2$ was added. The mixture was stirred at room temperature for 1 h, then was partitioned between ether and 2M NaOH solution. The ether layer was washed with 2M NaOH, saturated NaHCO$_3$ solution, and saturated NaCl solution, dried over MgSO$_4$, and concentrated. The residue was purified by silica gel chromatography using 10% ethyl acetate-hexane to afford 0.514 g (60%) of a colorless oil; $^1$H NMR (200 MHz, CDCl$_3$,w): 1.80–2.3 (m, 6H), 2.65–2.9 (m, 4H), 3.3 (m, 1H), 4.11 (t, J=7Hz, 2H), 4.28 (dd, J=6.5, 4Hz, 1H), 4.45 (dt, J=5.5, 1.5 Hz, 2H), 4.95 (ddd, J=7.5, 5.5, 5 Hz, 1H), 5.26 (dq, J=10.5, 1.5 Hz, 1H), 5.39 (dq, J=17, 1.5 Hz, 1H), 6 03 (ddt, J=17, 10.5, 5.5 Hz, 1H), 6.68 (s, 1H), 6.75 (s, 1H) 6.90 (m, 3H), 7.30 (m, 2H); FAB mass spectrum (m/e): 427 (100, M+H).

Step B: Preparation of (2S*,3S*) 2 (-2,3-dihydro 2-(1,3-dithianylmethyl)-3 (2-phenoxyethyl)-5-hydroxy-6-(2-propenyl)benzofuran A solution of 0.524 g (1.20 mmol) of (Example 7, Step B) in 10 mL of CH$_2$Cl$_2$ was cooled to 0° C. Then 1.5 mL of a 1.0M solution of BCl$_3$ in CH$_2$Cl$_2$ was added and the solution was stirred at room temperature for 30 min. The reaction was quenched with 10 mL of saturated NaHCO$_3$ solution and the mixture was partitioned between ether and water. The ether layer was washed with NaHCO$_3$ solution and saturated NaCl solution. The combined organic extracts were dried over MgSO$_4$ and concentrated to a colorless oil that afforded 0.345 g (67%) of white needles upon trituration with hexane; mp 71°–73° C.; $^1$H NMR (200 MHz, CDCl$_3$, w): 1.80–2.3 (m. 6H). 2.65–2.9 (m, 4H). 3.3 (m, 1H), 3.38 (m, 2H), 4.11 (t, J=7Hz, 2H), 4.28 (dd, J=6.5, 4Hz, 1H), 4.95 (ddd, J=7.5, 5.5, 5 Hz, 1H), 5.20 (m, 3H), 6.68 (s, 1H), 6.75 (s, 1H) 6.90 (m, 3H), 7.30 (m, 2H); FAB mass spectrum (m/e): 427 (100, M+H).

EXAMPLE 8

(2S*,3S*)-2-(-2,3-dihydro-2-(1,3-dithianylmethyl)-3-(2-phenoxyethyl)-5-hydroxy-6-propylbenzofuran A solution of 0.250 g (0.590 mmol) of (Example 7, Step B) and 50 mg of 5% Pd/C in 5 mL of ethyl acetate was shaken under 40 psi $H_2$ for 1h. The solution was filtered through Celite and the filtrate concentrated to a colorless oil. This was purified by HPLC (silica gel, Whatman Magnum 20) using 20% ethyl acetate-hexane to afford 0.191 g (77%) of colorless oil; $^1$H NMR (200 MHz, CDCl$_3$,w): 0.97 (t, J=6.5Hz, 3H), 1.60 (m, 2H), 1.80-2.3 (m, 6H), 2.5 (t, J=7Hz, 2H), 2.65-2.9 (m, 4H), 3.3 (m, 1H), 4.11 (t, J=7Hz, 2H), 4.28 (dd, J=6.5, 4Hz, 1H), 4.95 (ddd, J=7.5, 5.5, 5 Hz, 1H), 6.68 (s, 1H), 6.75 (s, 1H) 6.90 (m,3H), 7.30 (m, 2H); FAB mass spectrum (m/e): 429 (100, M+H,).

EXAMPLE 9

(2S*,3S*) 3-Butyl-2,3 dihydro-2 ethyl-5-hydroxy-6-(2-propenyl)benzofuran

Step A:
(2S*,3S*)-3-Butyl-2,3-dihydro-2-(2-(4-methylbenzenesulfonyloxy)ethyl)-5-(2-propenyloxy) benzofuran A solution of 0.985 g (3.56 mmol) of (Example 5, Step A) 1.34 g (7 mmol) of p-toluenesulfonyl chloride, and 2 mL of pyridine in CH$_2$Cl$_2$ was stirred at room temperature for 4h. The solution was partitioned between ether and water and the ether layer was washed with saturated NaHCO$_3$ solution and saturated NaCl, dried over MgSO$_4$, and concentrated. The oily residue was purified by chromatography on silica gel using 10% ethyl acetate-hexane to afford 1.32 g of an homogeneous oil; $^1$H, NMR (200 MHz, CDCl$_3$, w): 0.91 (t, J=7 Hz, 3H), 1.36 (m, 4H), 1.67 (m, 4H), 2.53 (s, 3H), 2.70 (s, 1H), 3.03 (dt, J=6, 5.5 Hz, 1H), 4.45 (dt, J=5.5, 1.5 Hz, 2H), 4.65 (t, J=6Hz, 2H), 4.82 (ddd, J=7.5, 5.5, 5 Hz, 1H), 5.26 (dq, J=10.5, 1.5 Hz, 1H), 5.39 (dq, J=17, 1.5 Hz, 1H), 6.03 (ddt, J=17, 10.5, 5.5 Hz, 1H), 6.68 (m, 2H), 6.75 (m, 1H), 7.40 (d, J=8 Hz, 2H), 8.10 (d, J=8Hz, 2H); FAB mass spectrum (m/e): 431 (100, M+H).

Step B: Preparation of (2S*,3S*) 3-Butyl-2,3-dihydro-2-ethyl-5-(2-propenyloxy)benzofuran A solution of 0.431 g (1.0 mmol) of (Example 9, Step A) and 2 mL of a 1M solution of lithium triethylborohydride in tetrahydrofuran was stirred at room temperature for 1h. The reaction was quenched with water and the solution was partitioned between ether and water. The ether layer was washed with saturated NaHCO$_3$ solution and saturated NaCl solution, dried over MgSO$_4$, and concentrated. The oily residue was dried under high vacuum for 24 h, then chromatographed on silica gel using 10% ethyl acetate-hexane to afford 0.245 g (94%) of a colorless oil; $^1$H NMR (200 MHz, CDCl$_3$, w): 0.91 (m, 6H), 1.36 (m, 4H), 1.67 (m, 4H), 3.03 (dt, J=6, 5.5 Hz, 1H), 4.45 (dt, J=5.5, 1.5 Hz, 2H), 4.82 (ddd, J=7.5, 5.5, 5 Hz, 1H), 5.26 (dq, J=10.5, 1.5 Hz, 1H), 5.39 (dq, J=17, 1.5 Hz, 1H), 6.03 (ddt, J=17, 10.5, 5.5 Hz, 1H), 6.68 (m, 2H), 6.75 (m, 1H); FAB mass spectrum (m/e): 261 (100, M+H).

Step C: Preparation of (2S*,3S*) 3-Butyl-2,3-dihydro-2-ethyl-5-hydroxy-6-(2-propenyl)-benzofuran A solution of 0.240 g (0.94 mmol) of (Example 9, Step B) in 5 mL of CH$_2$Cl$_2$ was cooled to 0° C. Then 1 mL of a 1.0M solution of BCl$_3$ in CH$_2$Cl$_2$ was added and the solution was stirred at 0° C. for 30 min. The reaction was quenched with 10 mL of saturated NaHCO$_3$ solution and the mixture was partitioned between ether and water. The ether layer was washed with NaHCO$_3$ solution and saturated NaCl solution. The combined organic extracts were dried over MgSO$_4$ and concentrated to afford 0.230 g (94%) a colorless oil; $^1$H NMR (200 MHz, CDCl$_3$,w): 0.91 (m, 6H), 1.36 (m, 6H), 1.67 (m, 2H), 3.03 (dt, J=6, 5.5 Hz, 1H), 3.35 (m, 2H), 4.82 (ddd, J=7.5, 5.5, 5 Hz, 1H), 5.17 (m, 3H), 6.68 (s, 1H), 6.75 (s, 1H); FAB mass spectrum (m/e): 261 (100, M+H).

EXAMPLE 10

(2S*,3S*)-3-Butyl-2,3-dihydro-2-ethyl-5 hydroxy-6-propylbenzofuran

A solution of 0.230 g (0.883 mmol) of (Example 9, Step C) and 50 mg of 5% Pd/C in 5 mL of ethyl acetate was shaken under 40 psi $H_2$ for 1h. The solution was filtered through Celite and the filtrate concentrated to 0.230 g (99%) of an homogeneous oil; $^1$H NMR (200 MHz, CDCl$_3$,w): 0.91 (m, 9H), 1.36 (m, 8H), 1.67 (m, 2H), 2.52 (t, J=6.5 Hz, 2H), 3.03 (dt, J=6, 5.5 Hz, 1H), 4.82 (ddd, J=7.5, 5.5, 5 Hz, 1H), 6.68 (s, 1H), 6.75 (s, 1H); FAB mass spectrum, (m/e): 263 (100, M+H,).

EXAMPLE 11

Methyl (2S*,3S*)-(3-ethyl-2-hydroxy-5-(2 propenyl)-2-benzofuranyl)acetate

EXAMPLE 12

Methyl (2S*,3S*)-(3-propyl-2,hydroxy-5-(2-propenyl)-2-benzofuranyl)acetate

EXAMPLE 13

Methyl (2S*,3S*)-(3-pentyl-2,hydroxy-5-(2-propenyl)-2-benzofuranyl)acetate

EXAMPLE 14

Methyl (2S*,3S*)-(3-hexyl-2,hydroxy-5-(2-propenyl)-2-benzofuranyl)acetate

Following the procedures of (Example 1, Steps A-D), but substituting an equivalent amount of n-butanal, n-pentanal, n heptanal and n-octanal for n-hexanal in (Step A of Example 1) you can obtain Examples 11 12 13 and 14 respectively.

EXAMPLE 15

Methyl (2S*,3S*) (3-ethyl-2-hydroxy-5-propyl-2-benzofuranyl)acetate

EXAMPLE 16

Methyl (2S*,3S*)-(3-propyl-2-hydroxy-5-propyl-2-benzofuranyl)acetate

EXAMPLE 17

Methyl (2S*,3S*) (3-pentyl-2-hydroxy-5-propyl-2-benzofuranyl)acetate

EXAMPLE 18

Methyl (2S*,3S*)-(3-hexyl-2-hydroxy-5-propyl-2-benzofuranyl)acetate

Following the procedure of Example 2 but substituting the compound of Examples 11, 12, 13, and 14 you can obtain Examples 15, 16, 17, and 18, respectively.

What is claimed is:

1. A compound of Formula I:

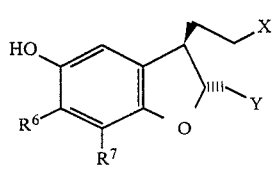

wherein:
R$^6$ is:
  (C$_3$–C$_6$)-1-alk-2-ene, or
  (C$_3$–C$_6$)-alkyl; and
R$^7$ is
  H;
X is:
  H,
  (C$_1$–C$_6$)-alkyl,
  phenoxy, or
  (C$_1$–C$_6$)-alkyloxyl; and
Y is
  (CH$_2$)$_n$CO$_2$CH$_3$, where n=0, 1, 2, 3, 4, or 5.

2. The compound of Formula I:

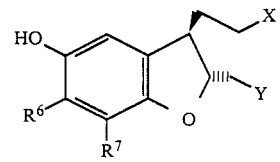

wherein:
R$^6$ is:
  n-propyl, or
  1-prop-2-enyl; and
R$^7$ is
  H,
X is:
  H,
  alkyl (C$_1$–C$_6$), or
  phenoxyl; and
Y is
  methoxycarbonyl, 3. A compound according to claim 1, selected from the group consisting of compounds of the Formula I wherein:
  (a) R$^6$ is 2-propenyl, R$^7$ is H, X is ethyl, and Y is
  (b) R$^6$ is n-propyl, R$^7$ is H; X is ethyl, and Y is methoxycarbonyl and
  (c) R$^6$ is 2-propenyl, R$^7$ is H, X is phenoxy, and Y is methoxycarbonyl and
  (d) R$^6$ is n-propyl, R$^7$ is H, X is phenoxy, and Y is methoxycarbonyl and
  (e) R$^6$ is 2-propenyl, R$^7$ is H, Y is methoxycarbonyl, and X is:
    (1) H,
    (2) CH$_3$,
    (3) n-propyl, or
    (4) n-butyl; and
  (f) R$^6$ is n-propyl, R$^7$ is H, Y is methoxycarbonyl, and X is:
    (1) H,
    (2) CH$_3$,
    (3) n-propyl, or
    (4) n-butyl.

4. A method of inhibiting mammalian leukotriene biosynthesis or action which comprises administering to a mammal a pharmaceutically effective amount of a compound of claim 1.

5. A method of claim 4 wherein the mammal is a human.

6. A method of treating pulmonary conditions, inflammation, cardiovascular conditions, or skin conditions which comprises administering to a human in need of such treatment a pharmaceutically effective amount of a compound of claim 1.

* * * * *